United States Patent [19]

Bortle

[11] 4,296,502
[45] Oct. 27, 1981

[54] SELF-PACKAGING URINE CONDUIT

[76] Inventor: Bonnie Bortle, 62 Newtonville Ave., Newton, Mass. 02158

[21] Appl. No.: 130,738

[22] Filed: Mar. 17, 1980

[51] Int. Cl.³ .......................... A61G 9/00; E03D 13/00; A47K 11/12

[52] U.S. Cl. .................................... 4/144.1; 4/144.2; 4/144.4; 128/761; 128/767; 141/337; 150/9

[58] Field of Search .............................. 4/144.1–144.4, 4/301, 307, 114.1; 150/1, 9; 46/87, 90; 141/337; 128/295, 760–763, 767; 222/528, 530

[56] References Cited

U.S. PATENT DOCUMENTS

| | | | |
|---|---|---|---|
| 901,134 | 10/1908 | Weidl | 4/144.3 X |
| 1,407,872 | 2/1922 | Lacy | 4/144.4 |
| 1,762,893 | 6/1930 | Saul | 150/9 X |
| 1,951,871 | 3/1934 | Judah | 4/144.3 X |
| 2,734,198 | 2/1956 | Kutsche | 4/144.3 X |
| 2,746,651 | 5/1956 | Lewis | 222/528 X |
| 2,895,654 | 7/1959 | Rieke | 222/530 X |
| 3,095,578 | 7/1963 | Stanford | 4/144.2 |
| 3,579,652 | 5/1971 | Ericson | 4/144.2 |
| 3,613,122 | 10/1971 | Gross et al. | 4/144.4 |
| 3,703,731 | 11/1972 | Leiser | 4/144.3 |
| 3,811,136 | 5/1974 | Whitney et al. | 4/144.1 |
| 3,822,419 | 7/1974 | Wilson, Sr. | 4/144.4 X |
| 3,956,778 | 5/1976 | Tanaka | 4/144.1 X |
| 3,964,111 | 6/1976 | Packer | 4/144.4 |
| 3,976,076 | 8/1976 | Beach | 4/144.1 X |
| 4,023,216 | 5/1977 | Li | 4/144.3 |

FOREIGN PATENT DOCUMENTS

| | | | |
|---|---|---|---|
| 1805572 | 2/1978 | Fed. Rep. of Germany | 4/144.4 |
| 2306674 | 11/1976 | France | 4/144.1 |
| 1443060 | 7/1976 | United Kingdom | 4/144.1 |

Primary Examiner—Stuart S. Levy

[57] ABSTRACT

A self packaging urine conduit for women comprises a flexible, reversibly deformable and fluid-tight tubular medial element, a relatively rigid tubular end piece connected to one end of the medial element to form a continuous fluid-tight channel therewith, a rim connected to the other end of the medial element, and a handle element connected to the rim. The rim has an undeformed dimension that is greater than the inner dimension of the end piece, but is resiliently deformable to fit within the end piece. The medial element is capable of being reversibly inverted for storage of the rim, the handle and the medial portion within the end piece. The conduit is maintained in packed condition by the pressure of the deformed rim against the inner surface of the end piece.

6 Claims, 7 Drawing Figures

SELF-PACKAGING URINE CONDUIT

This invention relates to a urine conduit for women. More specifically it relates to a self-packaging urine conduit.

Urine conduits for women are useful wherever standard toilet facilities are unavailable, such as on camping trips, in light aircraft or on small craft.

Urine conduits of various designs are known, but because of their shape and size the existing types of conduits have been inconvenient and awkward to carry about. It is therefore desirable to provide such an article that is compact and convenient to carry.

It is therefore an object of this invention to provide a urine conduit for women that is compact and convenient to carry. It is a further object to provide such an article that may be made of biodegradable material and therefore may be disposed of easily in situations such as camping trips, where non-degradable trash must be carried out by the camper.

According to the invention, a self packaging urine conduit for women comprises a tubular medial element, a tubular end piece, a rim and a handle element. The tubular medial element is flexible, reversibly deformable, and fluid-tight, and has a first portion of generally uniform inner dimension, and a second generally funnel-shaped portion continuous therewith. The funnel-shaped portion has an inner dimension increasing from that of the first portion to a rim dimension at its free edge.

The tubular end piece is relatively rigid and has an inner dimension approximately equal to that of the medial element first portion. The medial element first portion is connected to the tubular end piece to define at least one connecting area. The medial element first portion and the tubular end piece together form a continuous fluid-tight channel.

The rim is integrally connected to the medial element funnel-shaped portion at its free edge. The rim has an undeformed dimension that is greater than the inner dimension of the end piece, but is resiliently deformable to fit within the tubular end piece. The handle element, which is relatively rigid, is integrally and rigidly connected to the rim and is generally coplanar with the rim. The rim preferably has a generally elliptical undeformed shape, the handle being connected to the rim at one end of the major axis of the rim.

The medial element first portion has a length at least as great as the length of the tubular end piece. The medial element first portion is capable of being reversibly inverted for storage of the rim, the handle and the funnel-shaped portion within the tubular end piece.

In a preferred embodiment, the rim and the handle element in the deformed condition of the rim together have an overall length that is at least about as great as the length of the tubular end piece, so that the handle element can be manually grasped for unpacking of a self-packaged conduit.

In an alternative preferred embodiment, a flexible lead element is attached to the rim or to the handle element and is adapted to extend beyond the tubular end piece in the self-packaged condition of the conduit, whereby the flexible lead element can be manually grasped for unpacking of a self-packaged conduit.

The tubular element has an inflow end adjacent the rim and handle elements and an outflow end remote therefrom; a connecting area is adjacent the outflow end, a part of the medial element first portion lying within the tubular element to form a fluid-tight lining therethrough.

In another alternative preferred embodiment, the tubular element has an inflow end and an outflow end, the connecting area being adjacent the inflow end.

Other objects, features and advantages will appear from the following description of a preferred embodiment, together with the drawing, in which.

In the figures, thicknesses have been exaggerated with respect to linear dimensions, for clarity.

Figure 4:
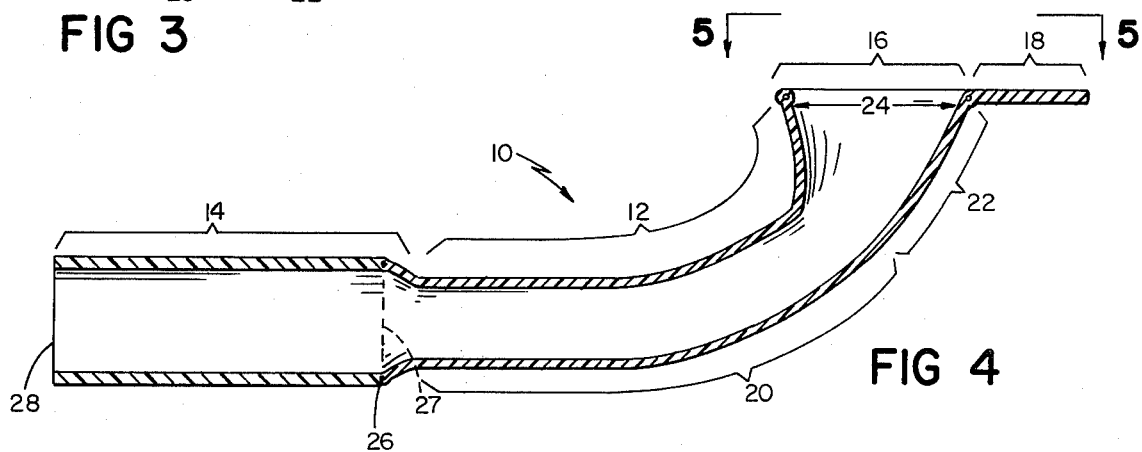
FIG. 4 is a cross sectional view of the unpacked conduit.

Referring now to the drawing, and in particular to FIG. 4, the conduit 10 of the invention comprises generally a medial element 12, an end piece 14, a rim 16 and a handle element 18.

Medial element 12 is flexible and reversibly deformable, being made of a light-weight, fluid-tight material such as thin rubber sheeting. Preferably, medial element 12 is made of a biodegradable material.

Medial element 12 comprises a first portion 20 of generally uniform inner dimension, preferably about three-quarters of an inch. Medial element first portion 20 has a length at least as great as the length of tubular end piece 14. Medial element 12 further comprises a second portion 22 that is generally funnel-shaped. Funnel-shaped portion 22 is continuous with first portion 20, and has an inner dimension increasing from that of the first portion to a rim dimension, indicated at 24 in FIG. 4, at its free edge. Rim dimension 24 is typically about three and one-half inches.

End piece 14, which is preferably made of a biodegradable material, is tubular and relatively rigid compared with medial element 12. End piece 14 is about six inches long and has an inner dimension approximately equal to that of medial element first portion 20. End piece 14 has an inflow end 27 and an outflow end 28. Medial element first portion 20 is connected to tubular end piece 14 in at least one connection area 26, so that medial element first portion 20 and end piece 14 together form a continuous fluid-tight channel.

Figure 1:
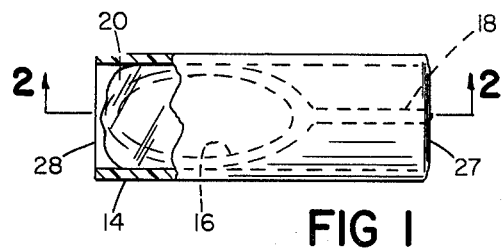
FIG. 1 is a cross-sectional view of the packaged conduit of the invention.
Figure 5:
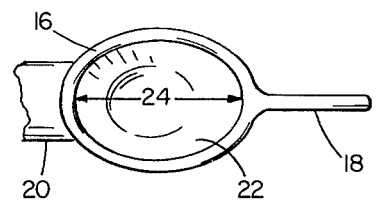
FIG. 5 is a detail plan view showing the rim and handle of the conduit in unpacked form.

Rim 16 is resiliently deformable, being made of light weight plastic or rubber, preferably biodegradable. Rim 16 is integrally connected to medial element funnel shaped portion 22 at the free edge of the latter. Rim 16 has an undeformed dimension greater than the inner dimension of end piece 14, but can be resiliently deformed to fit within end piece 14, as seen in FIG. 1. In preferred embodiments, rim 16 has a generally elliptical outline in its undeformed condition, as seen in FIG. 5, having dimensions of about three and a half inches by about two inches.

Handle element 18 is relatively rigid, and is rigidly connected to rim 16 at one end of the major axis of the elliptical form of rim 16. Handle element 18 is about two and one half inches long, and is generally coplanar with rim 16. In preferred embodiments, rim and handle are manufactured as a single element.

Figure 2:
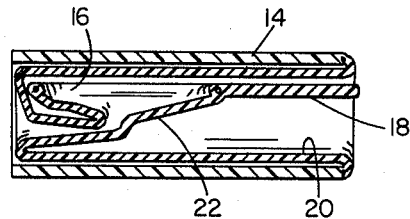
FIG. 2 is a cross sectional view of the packaged conduit of the invention, taken on line 2—2 of FIG. 1.

In the embodiment shown in FIG. 2, rim 16 and handle element 18 in the deformed condition of the rim together have an overall length that is at least about as great as the length of tubular end piece 14, which permits handle element 18 to be manually grasped in order to unpack the self-packaged conduit.

Figure 7:
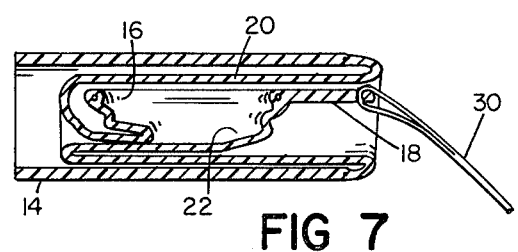
FIG. 7 shows an alternative construction of another portion of the conduit of the invention.

In an alternative embodiment shown in FIG. 7, the handle element 18 need not be within reach in the packaged condition of the conduit; a flexible lead element 30 is attached to handle element 18 and extends beyond tubular end piece 14, to permit unpacking of the self-packaged conduit. Lead element 30 could also be attached to rim 16 rather than to handle element 18.

In the embodiment shown in FIG. 4, medial element first portion 20 is connected to end piece 14 at connection area 26 at the inflow end 27 of end piece 14. In this embodiment, medial element 12 is about fifteen inches long overall, having a first portion 20 of about eight to nine inches in length. Tubular end piece 14 in this embodiment must be made of a fluid-tight material, such as a coated paper or cardboard.

Figure 6:
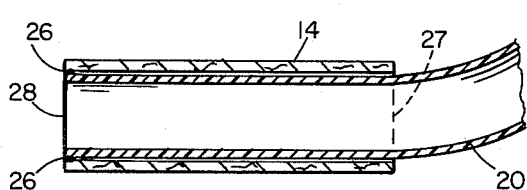
FIG. 6 shows an alternative construction of a portion of the conduit of the invention.

In an alternative embodiment shown in FIG. 6, medial element first portion 20 is connected to end piece 14 at least at the connection area 26 adjacent outflow end 28 of end piece 14. A part of medial element first portion 20 therefore lies within tubular element 14 to form a fluid-tight lining therethrough. In this embodiment, medial element 12 is about twenty-one inches long, of which about six inches lies within tubular element 14. In this embodiment, tubular end piece 14 need not be made of a fluid-tight material.

In packed condition of the embodiment shown in FIGS. 1 to 4, rim 16 is compressed and deformed to fit within end piece 14, and a part of medial element first portion 20 is inverted, or turned inside out, and presses against the inner walls of end piece 14. Rim 16 and handle 18 lie within portion 20. Rim 16, by pressing outwardly against the inner surface of end piece 14, maintains the conduit in packed condition.

In the embodiment shown in FIG. 6, part or all of medial element first portion 20 may simply be folded within tubular end piece 14. Rim 16, by pressing outwardly against the inner surface of end piece 14, maintains the conduit in packed condition.

Figure 3:
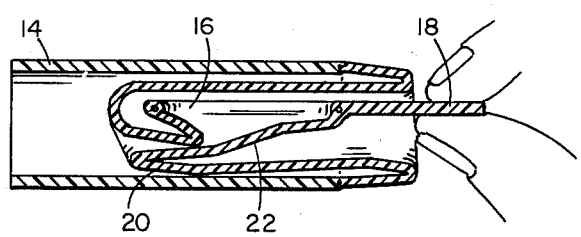
FIG. 3 is similar to FIG. 2 but shows the conduit partly unpacked.

As seen in FIG. 3, by pulling on handle element 18, the user unpacks the conduit from end piece 14. Rim 16 expands in its unpacked condition to the form shown in FIG. 5. In the embodiment shown in FIG. 7, the user unpacks the conduit by pulling on flexible lead element 30.

Preferably, the conduit is made entirely of a biodegradable material. As the conduit is self-packaging, nothing remains that cannot be disposed of conveniently. In its packed condition, the conduit is compact and easily carried.

What is claimed is:

1. A self packaging urine conduit for women, comprising
    a flexible and reversibly deformable fluid-tight tubular medial element, having a first portion of generally uniform inner dimension, and a second generally funnel-shaped portion continuous therewith and having an inner dimension increasing from that of said first portion to a rim dimension at its free edge,
    a relatively rigid tubular end piece having an inner dimension approximately equal to that of said medial element first portion, said medial element first portion being connected to said tubular end piece to define at least one connecting area, said medial element first portion and said tubular end piece together forming a continuous fluid-tight channel,
    a rim integrally connected to said medial element funnel-shaped portion at said free edge, said rim having an undeformed dimension greater than the inner dimension of said tubular end piece and being resiliently deformable to fit within said tubular end piece, and
    a relatively rigid handle element integrally and rigidly connected to said rim and generally coplanar with said rim,
    said medial element first portion having a length at least as great as the length of said tubular end piece,
    said medial element first portion being reversibly inverted for storage of said rim, said handle and said funnel shaped portion within said tubular end piece.

2. The conduit of claim 1 wherein said rim and said handle element in the deformed condition of said rim together have an overall length that is at least about as great as the length of said tubular end piece, whereby said handle element can be manually grasped for unpacking of a self-packaged said conduit.

3. The conduit of claim 1, further comprising a flexible lead element attached to said handle element and adapted to extend beyond said tubular end piece in the self-packaged condition of said conduit, whereby said flexible lead element can be manually grasped for unpacking of a self-packaged said conduit.

4. The conduit of claim 1, said tubular element having an inflow end adjacent said rim and handle elements and an outflow end remote therefrom, a said connecting area being adjacent said outflow end, a part of said medial element first portion lying within said tubular element to form a fluid-tight lining therethrough.

5. The conduit of claim 1, said tubular element having an inflow end and an outflow end, said connecting area being adjacent said inflow end.

6. The conduit of claim 1, said rim having a generally elliptical undeformed shape, and said handle being connected to said rim at one end of the major axis of said rim.

* * * * *